United States Patent [19]
DiGuiseppi et al.

[11] Patent Number: 5,858,769
[45] Date of Patent: *Jan. 12, 1999

[54] DEVICE FOR DETECTING MICROORGANISMS

[75] Inventors: James L. DiGuiseppi; Thurman C. Thorpe, both of Durham, N.C.

[73] Assignee: Akzo Nobel N.V., Arnhem, Netherlands

[*] Notice: This patent issued on a continued prosecution application filed under 37 CFR 1.53(d), and is subject to the twenty year patent term provisions of 35 U.S.C. 154(a)(2).

The term of this patent shall not extend beyond the expiration date of Pat. No. 5,164,796.

[21] Appl. No.: 648,602

[22] Filed: May 15, 1996

Related U.S. Application Data

[63] Continuation-in-part of Ser. No. 464,014, Jun. 5, 1995, abandoned, which is a continuation-in-part of Ser. No. 410,374, Mar. 24, 1995, Pat. No. 5,518,895, which is a continuation of Ser. No. 92,537, Jul. 14, 1993, abandoned, which is a continuation-in-part of Ser. No. 914,287, Jul. 14, 1992, abandoned, which is a continuation of Ser. No. 649,147, Feb. 1, 1991, Pat. No. 5,164,796, which is a continuation of Ser. No. 351,476, May 15, 1989, abandoned.

[51] Int. Cl.⁶ .................................................... C12M 1/34
[52] U.S. Cl. ..................................... 435/287.3; 435/286.2; 435/287.5; 435/288.1; 435/288.7
[58] Field of Search ................................ 435/32, 34, 39, 435/40, 286.2, 287.3, 287.5, 288.1, 288.7, 303.1, 304.1, 807, 808; 422/64, 82.05, 82.09; 356/39, 428, 426, 445; 250/328

[56] References Cited

U.S. PATENT DOCUMENTS

| | | |
|---|---|---|
| Re. 31,879 | 5/1985 | Lübbers . |
| 2,880,070 | 3/1959 | Gilbert . |
| 3,067,015 | 12/1962 | Lawdermilt . |

(List continued on next page.)

FOREIGN PATENT DOCUMENTS

| | | |
|---|---|---|
| 472420 | 2/1973 | Australia . |
| 0104463 | 4/1984 | European Pat. Off. . |
| 0117274 | 9/1984 | European Pat. Off. . |
| 0255087 | 2/1988 | European Pat. Off. . |
| 0301699 | 2/1989 | European Pat. Off. . |
| 033253 | 9/1989 | European Pat. Off. . |
| 0609986 | 8/1994 | European Pat. Off. . |
| 2603685 | 3/1988 | France . |
| 57-207861 | 12/1985 | Japan . |
| 61-149818 | 7/1986 | Japan . |
| 8100304 | 2/1981 | WIPO . |

OTHER PUBLICATIONS

"Optical Sensors for pH and Blood Gas Analysis," Marsoner et al., IFCC Workshop, Helsinki, 1985.

"Simplex Optimization of a Fiber–Optic Amonia Sensor Based on Multiple Indicators," Rhines et al., 60 Anal. Chem. 76–81 (1988).

"Fiber–Optic Fluorescing Sensor for Ammonia," Wolfbeiss et al., 185 Analytica Chemica ACTA, 321–327 (1986).

McFaddin, *Biochemical Tests for Identification of Medical Bacteria*, pp. 187–193 and 108–117 (1976).

*Primary Examiner*—William H. Beisner
*Attorney, Agent, or Firm*—Gregory R. Muir

[57] ABSTRACT

An apparatus and method for mixing/agitating microorganism culture bottles includes a wheel in which culture bottles are placed, with the wheel being set at an angle from vertical so that bottles are not inverted during rotation. A sensor such as a florescence or colorimetric sensor for carbon dioxide is disposed along the flat bottom surface of each of the bottles. Once during each revolution the bottles pass across a photodiode/light emitting diode pair (for a calorimetric system). A sensor transmits light emitted by the LED to the photodiode. At the same instant, an infrared reflective objective sensor, emitting on a digital rotary encoder, determines the bottle number. The change in sensor transmittance is directly related to cell growth so that bottles positive for growth can be detected by suitable software.

1 Claim, 16 Drawing Sheets

U.S. PATENT DOCUMENTS

| | | |
|---|---|---|
| 3,676,679 | 7/1972 | Waters . |
| 3,754,866 | 8/1973 | Ritchie et al. .............................. 422/64 |
| 3,853,712 | 12/1974 | House et al. . |
| 3,998,591 | 12/1976 | Eckfeldt . |
| 4,004,981 | 1/1977 | Hurni et al. . |
| 4,073,691 | 2/1978 | Ahnell et al. . |
| 4,101,383 | 7/1978 | Wyatt et al. . |
| 4,152,213 | 5/1979 | Ahnell . |
| 4,182,656 | 1/1980 | Ahnell et al. . |
| 4,236,211 | 11/1980 | Arvesen . |
| 4,271,123 | 6/1981 | Curry et al. ............................... 422/64 |
| 4,271,973 | 6/1981 | Quagliaro et al. ...................... 215/308 |
| 4,289,248 | 9/1981 | Lynn . |
| 4,293,643 | 10/1981 | Ohtake et al. . |
| 4,306,877 | 12/1981 | Lubbers . |
| 4,330,622 | 5/1982 | Desai . |
| 4,407,959 | 10/1983 | Tsuji . |
| 4,456,380 | 6/1984 | Kondo et al. . |
| 4,476,870 | 10/1984 | Peterson et al. . |
| 4,557,900 | 12/1985 | Heitzmann . |
| 4,568,518 | 2/1986 | Wolfbeis . |
| 4,672,039 | 6/1987 | Lundblom . |
| 4,698,308 | 10/1987 | Ikeda . |
| 4,780,191 | 10/1988 | Romette et al. . |
| 4,784,947 | 11/1988 | Woeller . |
| 4,824,789 | 4/1989 | Yafoso et al. . |
| 4,833,091 | 5/1989 | Leader et al. . |
| 4,871,676 | 10/1989 | Yamada . |
| 4,889,992 | 12/1989 | Hoberman . |
| 4,940,332 | 7/1990 | Miwa et al. ......................... 435/288.7 |
| 4,971,900 | 11/1990 | Ahnell . |
| 5,047,331 | 9/1991 | Swaine et al. . |
| 5,094,955 | 3/1992 | Calandra et al. . |
| 5,164,796 | 11/1992 | Di Guiseppi et al. ................ 435/288.7 |
| 5,232,839 | 8/1993 | Eden et al. . |
| 5,397,709 | 3/1995 | Berndt .................................. 435/288.7 |
| 5,498,543 | 3/1996 | Berndt .................................. 435/287.3 |
| 5,516,692 | 5/1996 | Berndt .................................. 435/288.7 |
| 5,518,923 | 5/1996 | Berndt et al. ........................ 435/287.3 |

DEVICE FOR DETECTING MICROORGANISMS

CROSS-REFERENCE TO RELATED APPLICATIONS

This is a continuation-in-part of application Ser. No. 08/464,014, filed Jun. 5, 1995 now abandoned, which is a continuation-in-part of application Ser. No. 08/410,374, filed Mar. 24, 1995, now U.S. Pat. No. 5,518,895, which is a continuation of application Ser. No. 08/092,537, filed Jul. 14, 1993, now abandoned, which is a continuation-in-part of application Ser. No. 07/914,287, filed Jul. 14, 1992, now abandoned, which is a continuation of application Ser. No. 07/649,147, filed Feb. 1, 1991, now U.S. Pat. No. 5,164,796, which is a continuation of application Ser. No. 07/351,476, filed May 15, 1989, now abandoned. This application is also related to U.S. Pat. No. 5,217,876, to Turner et al. (issued Jun. 8, 1993); U.S. Pat. No. 5,094,955, to Calandra et al. (issued Mar. 10, 1992); U.S. Pat. No. 5,314,855, to Thorpe et al. (issued May 24, 1994); and U.S. Pat. No. 4,945,060, to Turner et al. (issued Jul. 31, 1990), all of which patents are incorporated herein by reference.

The present invention provides a method and device for detecting/monitoring changes in pH, gas production ($CO_2$, $NH_2$, $H_2S$, etc.) or volatile acid production of a specimen using a growth medium and a sealed container without entering the container after the sample is prepared and added to the container. A sensor is provided which changes due to differences in concentrations of gas, volatile acid and/or pH within the vessel (e.g., within the medium in the vessel). In the present invention, a rotating wheel is provided for rotating a plurality of containers so as to agitate the medium within the containers and so as to move a plurality of containers past a detector which detects changes in the sensor disposed within each container.

BACKGROUND OF THE INVENTION

The presence of microorganisms in clinical specimens is conventionally determined by culturing the specimens in the presence of nutrients and detecting microbial activity through changes in the specimen or in the atmosphere over the specimen after a period of time. For example, in U.S. Pat. No. 4,182,656 to Ahnell et al. the sample is placed in a container with a culture medium comprising a carbon 13 labelled fermentable substrate. After sealing the container and subjecting the specimen to conditions conducive to biological activity, the ratio of carbon 13 to carbon 12 in the gaseous atmosphere over the specimen is determined and compared with the initial ratio. In U.S. Pat. No. 4,152,213, a method is claimed by which the presence of oxygen consuming bacteria in a specimen is determined in a sealed container by detecting a reduction in the amount of oxygen in the atmosphere over the specimen through monitoring the pressure of the gas in the container. U.S. Pat. No. 4,073,691 provides a method for determining the presence of biologically active agents, including bacteria, in a sealed container containing a culture medium by measuring changes in the character of the gaseous atmosphere over the specimen after a period of time. A method for non-invasive detection of $CO_2$ changes in the gaseous atmosphere is taught by Suppman et al., as disclosed in EPO application 83108468.6, published Apr. 4, 1984. The methods and apparatus described in these and other publications all require either a radiometric method or the invasion of the sealed container to measure changes in the gaseous atmosphere after culturing or require special materials that permit infra-red light to pass.

Other known methods for measuring microbial presence in specimens, particularly blood cultures, include measuring minute changes in temperature, pH, turbidity, color, bioluminescence, and impedance. Generally, these methods determine microbial presence or growth by detecting bacterial metabolic byproducts. Microbial presence may also be assessed by subculturing and/or staining. Of these methods, only impedance, radiometry and infra-red spectrometry provide the possibility of automated processing of clinical specimens. And except for impedance and infra-red measurements, these procedures also require entering the container in order to make a measurement on the liquid specimen or the gaseous atmosphere over the specimen. In addition to the likelihood of contamination and creating the likelihood of altering the constituency of the atmosphere over the specimen each time a determination is made, these methods do not permit taking measurements continuously or repeatedly over short time intervals for an extended period of time. This is a significant disadvantage as the growth rate of organisms differs depending on the organism and the number of organisms in the original sample, such that it cannot be predicted when detectable changes in the atmosphere or fluid sample will be presented. In a related problem, when organism growth is determined by pH changes in the liquid sample, various metabolic products will affect the pH of the sample differently. For example, the production of ammonia will raise the pH while the production of $CO_2$ will lower it. Different growth rates of different organisms could result in a pH increase at one time and a decrease at another time, which would not be detected if the pH is measured at widely spaced intervals. Another source of error when detecting changes by pH measurement in whole blood samples, particularly when an indicator dye is the means for pH determination, is the likelihood that the dye appearance can be affected or obscured by the presence of blood cells. Colorimetric indicators can only be effectively used if errors induced by the nature of the specimen can be prevented from influencing the appearance of the dye.

When the biologically active agent is an aerobic organism, a system must be provided for ensuring sufficient oxygen within the vessel so that biological activity can take place. One way of providing oxygen to the vessel is by adding oxygen to the atmosphere within the vessel containing the culture medium, at the time of manufacture of the vessel. Then, when a specimen is added to the vessel by the user of the vessel, oxygen will already be present within the vessel. Alternatively, a gas permeable membrane can be provided, such as within the cap of the vessel.

In order to overcome the problems associated with invasive measurement methods, measurement systems have been developed which utilize a sensor disposed inside the vessel. The sensor undergoes a change due to changes in amounts of a particular metabolic product or food source of the microorganisms. The sensor can be constructed so as to respond to changes within the vessel, thereby changing, for example, in color or fluorescence intensity. In the conventional fluorometric or colorometric measurement systems, a sensor which changes in color or fluorescence intensity is disposed on the inside of the culture bottle along the flat bottom surface of the bottle. A light source such as a light emitting diode can be provided proximate to the flat bottomed surface of each bottle, along with a detector for detecting changes in color or fluorescence. However, when an individual light source and detector are provided for each culture bottle, a degree of non uniformity is introduced and can result in errors of measurement.

In order to address this concern, rotatable culture systems have been proposed whereby a plurality of culture bottles are rotated past the same light source/sensor. For example, in U.S. Pat. No. 4,293,643 to Ohtake et al., a rotary culturing and measuring system is disclosed where L-shaped culture tubes are disposed radially around a rotatable drum at equal intervals. The drum (turntable) is disposed at an angle to horizontal, and a central shaft is driven to continuously or intermittently index the drum. Due to the movement of the drum, the substance being cultured is shaken. At a particular position along the wheel, the growth of the substance being cultured in the L-shaped culture tubes, is measured. A light source and a photodetector are disposed on opposite sides when one part of the L-shaped culture tube passes. While the drum turns, the turning motion allows for the use of a single light source and sensor to obtain the measured concentration values signal at every fixed time (or the degree of growth of a microorganism can be observed over a particular time interval).

In published European patent application EP 609986, a plurality of vials for culturing microorganisms are placed in a drum and rotated about an axis. Agitation results from placing the axis of rotation perpendicular to the force of gravity. A single light source and detector are provided (for each detection method) such that a plurality of vials may utilize a common light source and sensor.

SUMMARY OF THE INVENTION

The present invention relates to an apparatus and method for agitating containers for culturing microorganisms. The containers contain a sterile growth medium in a sterile container at least one part of which is transparent. Adjacent to the transparent part of the container, on the inside, is a disposed sensor which undergoes changes caused by changes within the container due to depletion or production of substances from the growth of microorganisms. Among other things, the sensor within each container may change in color or fluorescence intensity, which change is detected by a detector disposed along the path of rotation of the containers. The plurality of containers rotate past the detector such that a single detector can be utilized for detecting changes within sensors disposed within a plurality of containers.

In the present invention, liquid spills are better contained than in a conventional rotary apparatus, which containment is particularly desirable when biohazardous materials are involved. Also in the present invention, sensor readings are less prone to error as the angle of the sensor does not vary in relation to the detector. Further, in the present invention, a higher density of containers can be achieved in comparison to conventional rotary culturing systems.

This drawing shows the overall appearance of the functional part of the instrument, the detector assembly, with (1) a vessel passing the detector assembly, (2) sensor, (3) culture medium, the (4) light source, (5) photodetector, and the associated electronics including (6) current source, (7) current to voltage converter and (8) low pass filter.

In one embodiment, each detector assembly consists of a photodiode in a countersunk hole and one or more LED's arrayed such that light falls on the surface to be viewed, but not directly onto the detector itself. The electronic circuits in this embodiment include amplifiers and filters to condition the signals from the detectors, multiplexers to select among the signals available, and constant current sources for the illuminators.

Figure 1:
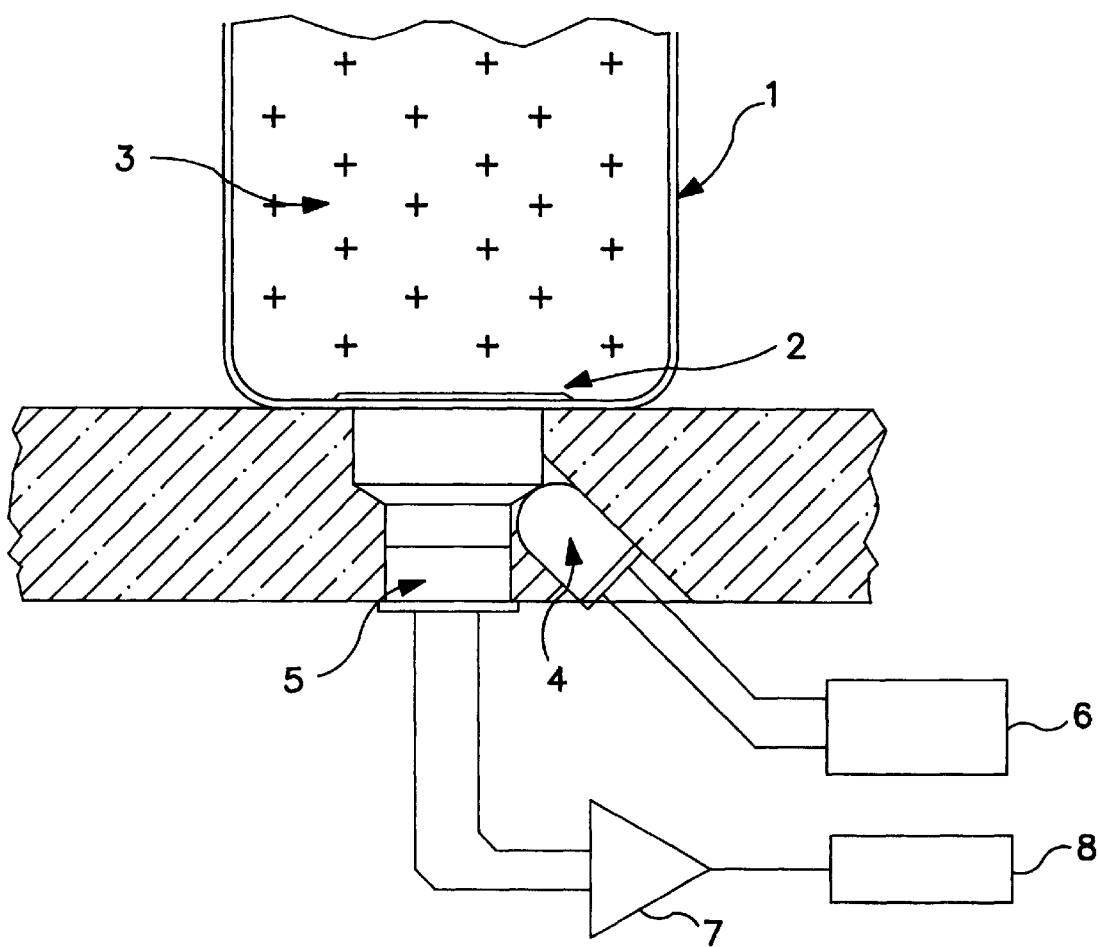
FIG. 1—Blood culture instrument
Figure 2:
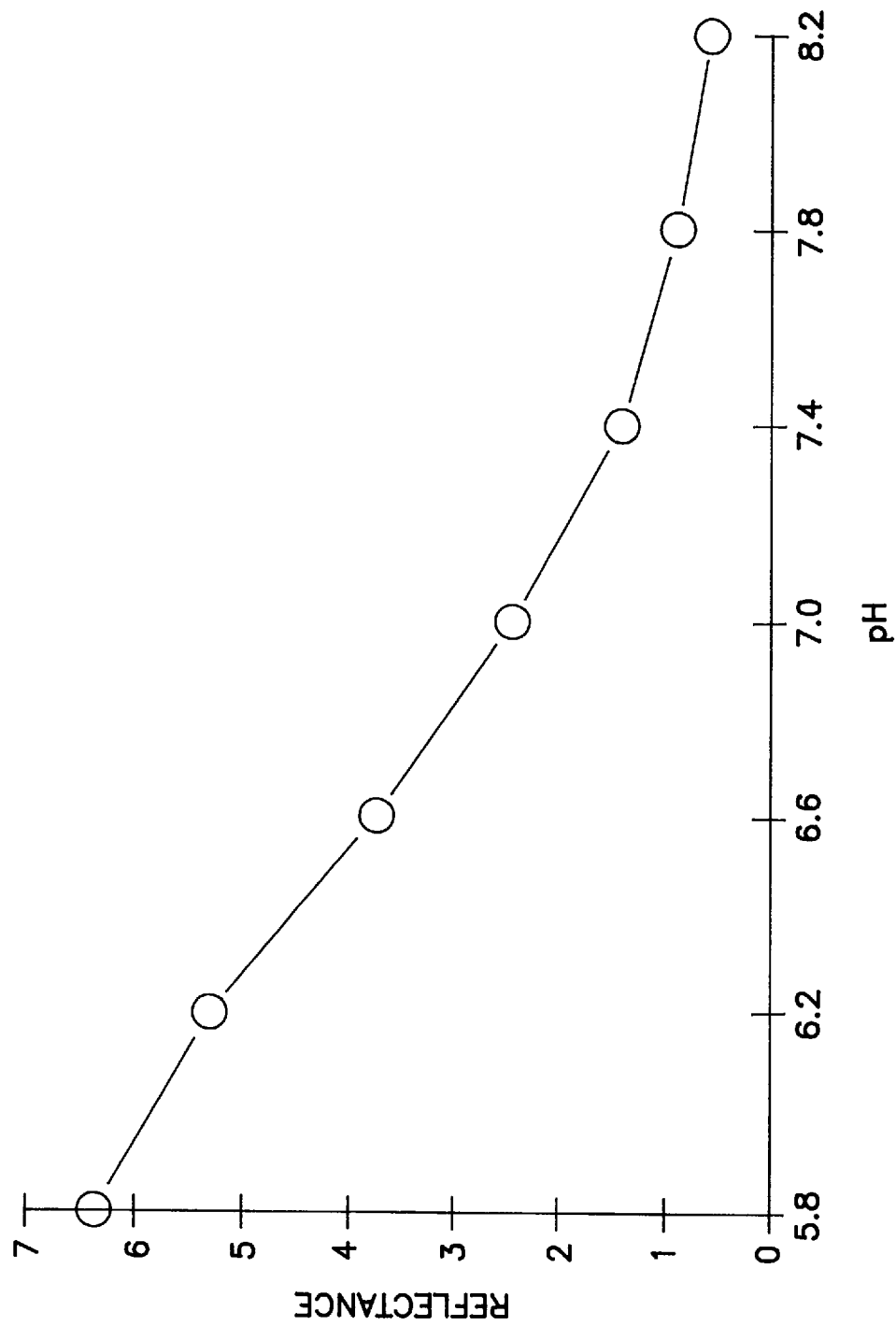

FIG. 2—pH Sensitivity

Besides testing the instrument subjectively with various colored bottles, it was tested with the pH sensitive membrane bottles. This figure shows the average voltage output of seven different detectors after equilibration of the sensor with various buffers over a pH range of 5.8 to 8.2. Detailed studies showed that the system could reliably distinguish changes of 0.1 pH unit over a range of pH 6.0 to 7.5.

Figure 3:
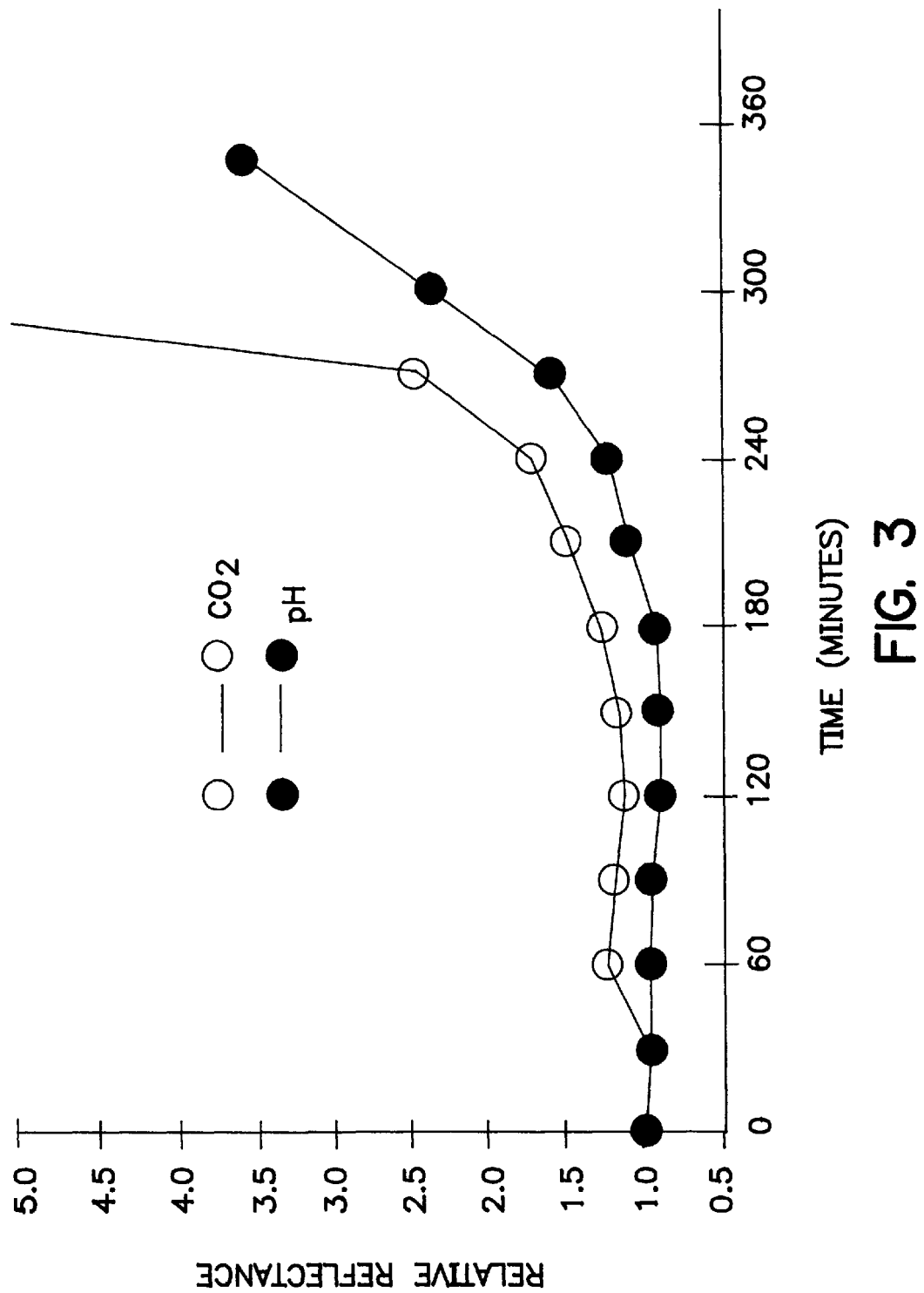

FIG. 3—pH and atmosphere change with microbial growth

The instrument was used to detect microbial growth by both pH change and by gas or volatile production. This figure shows the change in pH and in $CO_2$ resulting from growth of the bacterium, E. coli.

Figure 4:
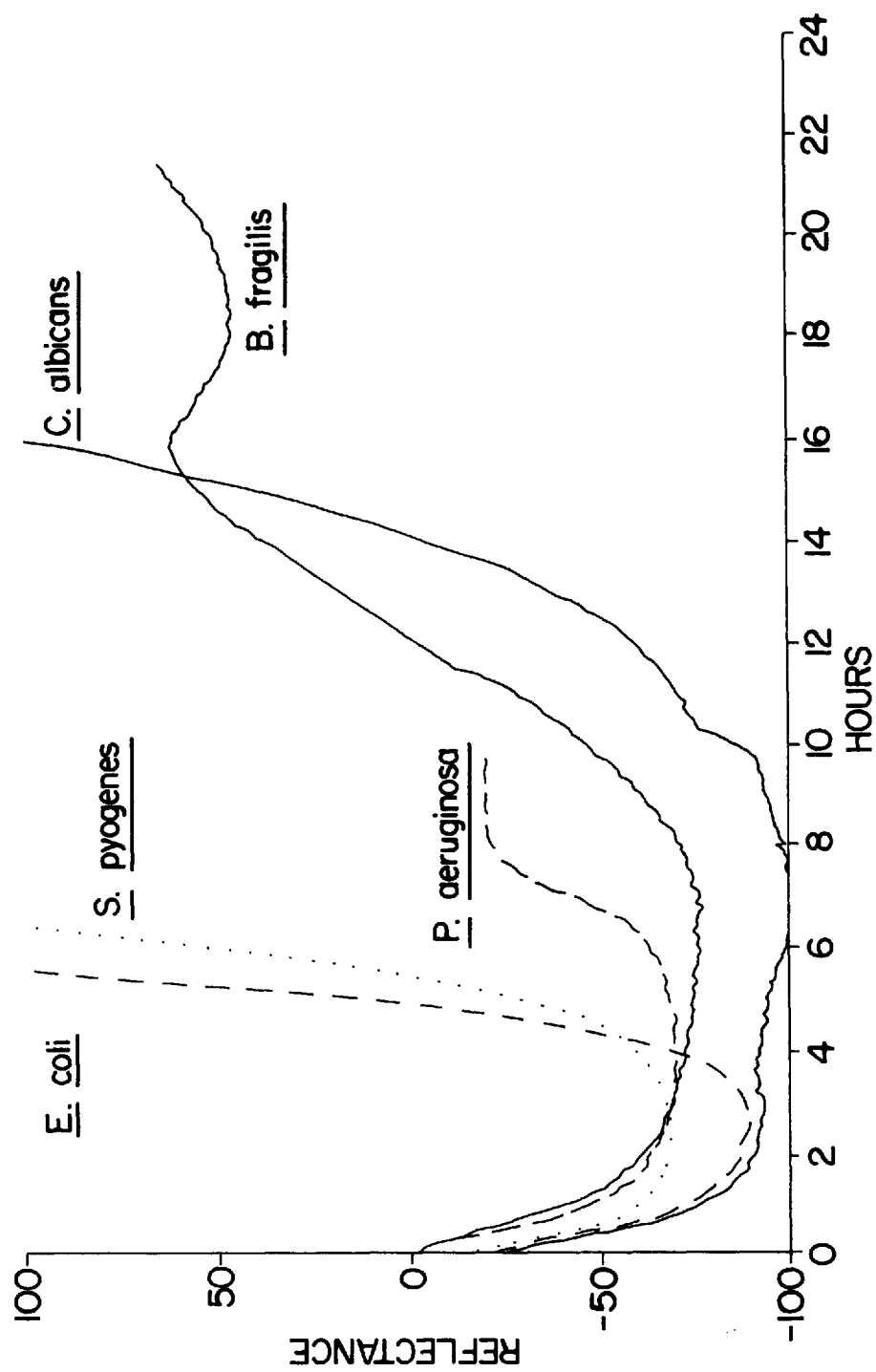

FIG. 4—Detection of a variety of microorganisms

Essentially all organisms will release gases or volatile acids in the course of their metabolism. Thus, this system can be used to detect the growth of a very wide range of microorganisms. This figure shows the detection of gases ($CO_2$) and/or volatile acids produced during the growth of E. coli, a Gram negative bacterium; S. pyogenes, a Gram positive bacterium; P. aeruginosa, a Gram negative non-fermenting bacterium; B. fragilis, an anaerobic bacterium; and C. albicans, a yeast. The units indicate relative gas concentration in the medium based on $CO_2$ concentration at the beginning of the assay. Because the sample containers and media are at room temperature (approximately 20° C.), and the container and sample are incubated at 37° C. during the assay, $CO_2$ is released into the space above the liquid sample and medium during the first 2 to 4 hours because of the reduced solubility of $CO_2$ in the liquid as temperature increases. Unless the containers and media are maintained at the higher temperature before introduction of the sample and placement into the instrument, reliable indication of the presence of microorganisms cannot be measured until after the minimum $CO_2$ concentration is passed, typically within the first 2 to 4 hours.

FIG. 5—

This is an illustration of a side view of the rotary apparatus with different sized bottles held between parallel plates.

FIG. 6a—

This is a top view of the rotating portion of the rotary mixer.

FIG. 6B—

This is a side view showing parallel plates (held together with pins) for holding culture bottles.

FIG. 7—

This is a side view of the rotary apparatus illustrating a plurality of culture bottles held in place and detectors for detecting changes in the culture bottles.

FIG. 8—

This is a modular concept for a bank of rotary mixers.

Figure 9A:
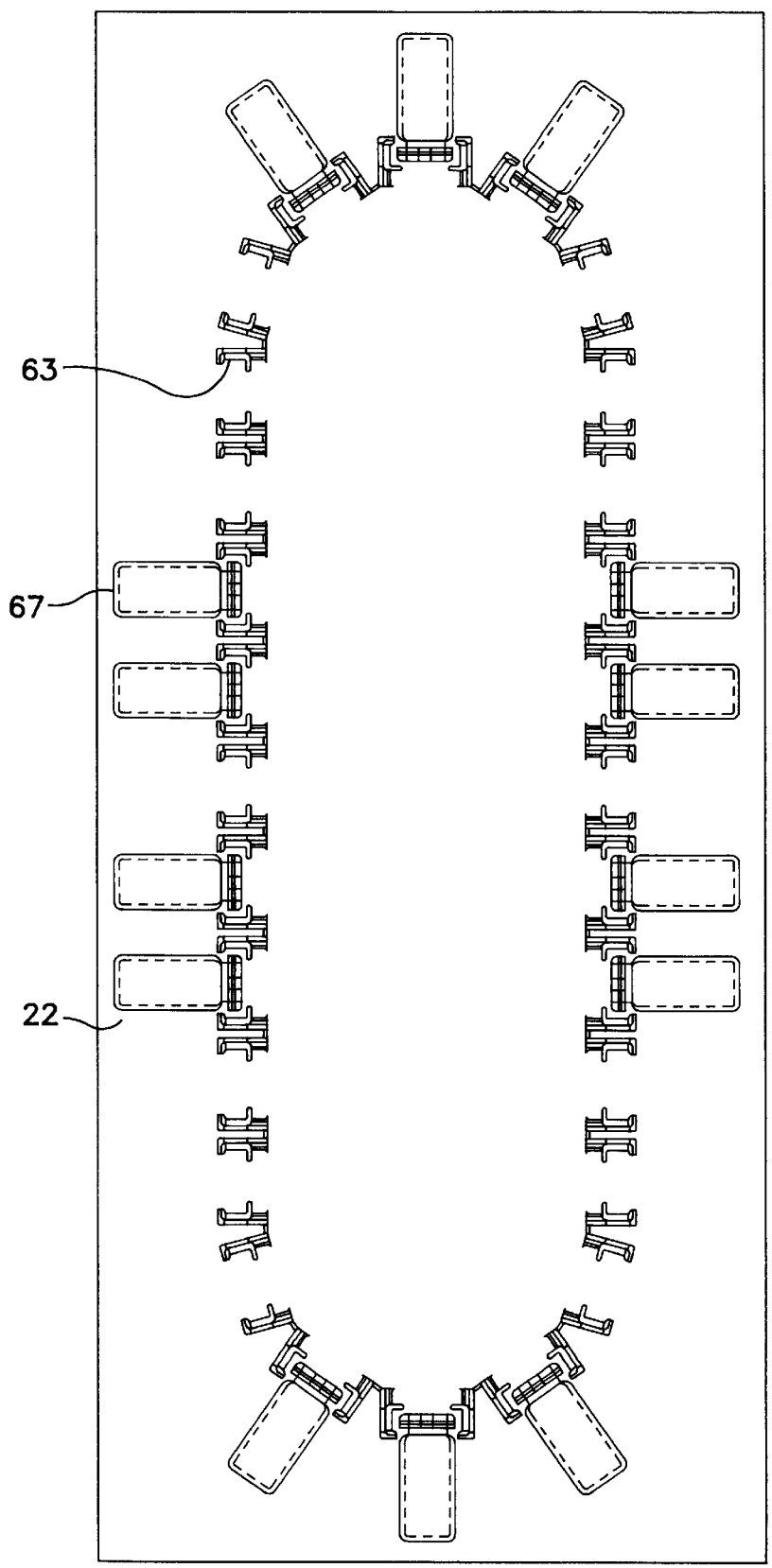
Figure 9B:
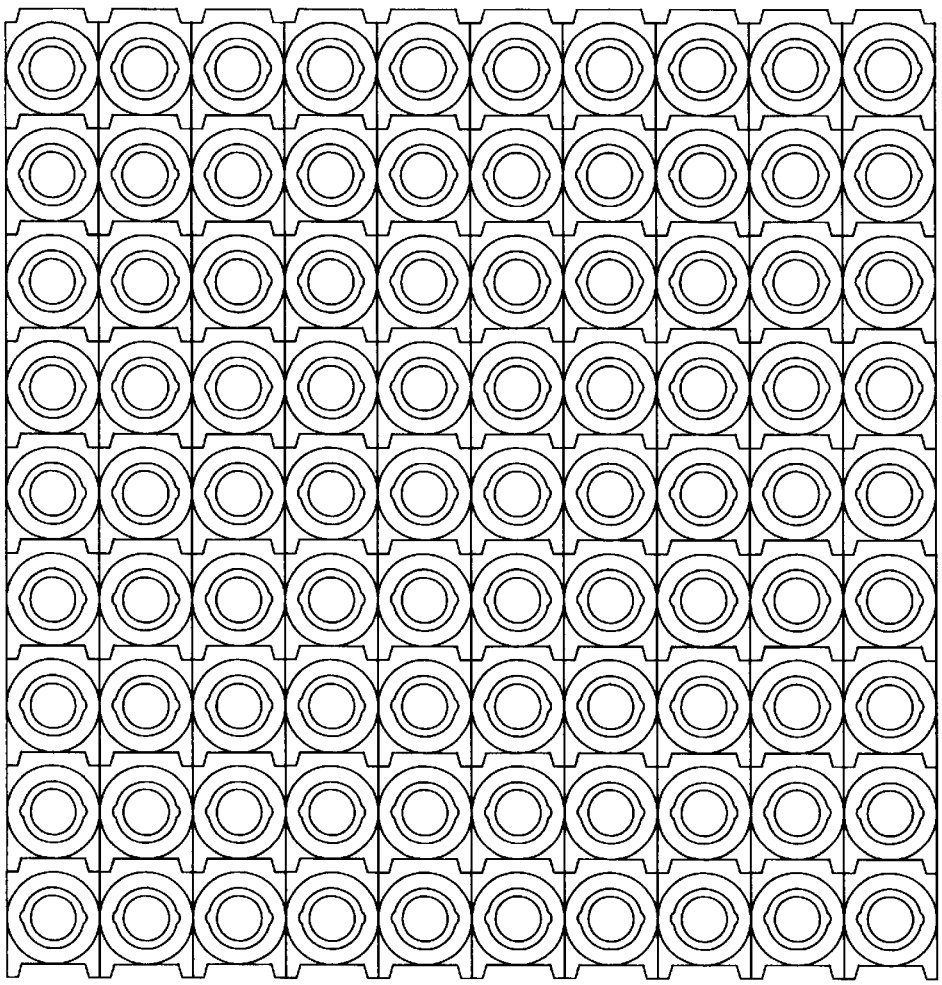

FIGS. 9a and 9B—

These are cross sectional and top views, respectively, of a second embodiment of the rotary mixer.

FIG. 10—

This is a circuit diagram for a photodiode amplifier for use in the invention.

FIG. 11—

This is a view of an optical encoder wheel for placement on the bottom plate of the rotating portion of the rotary apparatus.

FIG. 12—

This is a diagram of a circuit for optically encoding bottle position with a photomicrosensor.

FIG. 13—

This is a circuit diagram of a double-pole Bessel filter.

FIG. 14—

This is a graph showing the growth of *Candida albicans* in a culture bottle placed in the rotary mixer for culturing.

FIG. 15—

This is a graph showing the growth of *P. aeruginosa* and a base line of a sterile bottle.

FIG. 16—

This is an illustration of a top view of the rotary portion of the apparatus which shows the high density of culture bottles obtainable in the present invention.

DESCRIPTION OF PREFERRED EMBODIMENTS

The apparatus and device of the invention provide a non-invasive means for detecting the presence of microorganisms in clinical specimens, such as blood samples or other body fluids, and in non-clinical specimens by measuring an increase in metabolic products produced by microorganisms (or a decrease in a metabolic food source). The specimen is added to a specially formulated medium that enhances the production of certain microbial metabolic products, which are detected by a unique disposable sensor located at the bottom of a culture container or in the sealing means of the container. The sensor comprises a solid composition or membrane, which is referred to as an attachment or support medium, with an indicator medium immobilized on or within it. The sensor is located flush against the inside surface of a container, in the sealing means used to seal the container or attached to the sealing means, such that the indicator medium is visible from outside. It may be affixed to the container to prevent cells, proteins, other solids or other opaque or colored components from getting between it and the container surface. In certain embodiments the sensor is separated from the specimen and its growth medium by a membrane or solid layer that permits the passage of gas molecules but prevents passage of ions.

One embodiment of this invention comprises a sealing means, such as a cap or lid, which may be transparent or which may have a transparent section. The sensor can be placed in proximity to the transparent cap or section of cap or is made part of the cap. When the cap is used to seal the container, the changes in indicator are read through the transparent sealing means. An advantage seen to this embodiment is that this may be the most economical way to produce the containers on a large scale.

The sealing means may also be made of a material, such as a polymer, which contains encapsulated indicator micelles. A transparent section in either the container or the sealing means is not needed, as long as the material is permeable to the metabolic products of the microorganisms and the changes in the indicator are visible on the surface of the sealing means.

Microorganisms in specimens of body fluids, such as blood, containing as few as 1 organism per milliliter, can be detected using this invention. Such specimens may require up to 7 days incubation before the population of organisms reaches a critical level and where an increase in metabolic products can be measured. We found a concentration of $10^6$ CFU/ml for certain types of organisms provided measurable changes in pH or $CO_2$. All organisms showed measurable results at concentrations of $10^7$ to $10^8$ CFU/ml.

The sensor is useful in that: 1) the microbial metabolic products are measured in the liquid phase of the culture bottle rather than in the atmosphere over the specimen, 2) because the sensor is affixed to the interior surface of the bottle or the closure or sealing means or attached through the outside of the closure or sealing means, measurements can be made from outside the transparent wall of the bottle or the sealing means without having to violate the integrity of the bottle, 3) the external measurements can be made by visual inspection or with an instrument that measures by reflectance, 4) opaque or colored components in the specimen do not interfere with the ability of the sensor to detect changes or the measurement of those changes, and 5) a high concentration of indicator molecules is maintained within a small volume in the sensor, i.e., within the polymer emulsion or on the membrane, such that a color change can be easily observed.

The nutritional components that make up a complex microbial medium influence the metabolic pathways used by microorganisms. organic acids, bases and various gases are produced in proportions dependent on the nutrients available. These products also vary from species to species of microorganism. The presence of these products in the liquid medium can change its pH. The sensors used in the invention can contain pH sensitive indicators that give a measurable change in response to a pH change in the environment. In the embodiment in which the pH sensor is covered by a gas-permeable, ion-impermeable membrane, the presence of gases that affect the pH of the indicator, such as $CO_2$, is measured. Thus, microbial growth can be detected either directly or indirectly by measurement of gases dissolved in the medium. Carbon dioxide is a common metabolite produced by most organisms and, therefore, is the preferred metabolite for detection of microbial growth.

$CO_2$ and pH sensors share two common components, a molecular species useful as a pH indicator and an attachment/support medium. The pH indicator can be attached either covalently or non-covalently to the support medium. Alternately, the indicator can be encapsulated within a polymer matrix such as being emulsified within a polymer matrix prior to curing. To perform as a pH sensor, indicator must be in contact with the liquid medium. The $CO_2$ sensor has a third component, a semi-permeable substance that completely separates the indicator membrane from the specimen and growth medium. The semi-permeable layer may be a separate membrane, alternatively, the cured polymer adjacent to the specimen and growth medium may form an integral semi-permeable membrane. These sensors are affixed inside a suitable transparent vessel or a transparent sealing means with an appropriate adhesive. They may also comprise an integral part of the sealing means or be affixed to the sealing means or within the vessel as an indicator emulsified within a polymer matrix cured in situ. They can also be placed outside the container, as long as a method is provided that allows the metabolic products of the microorganisms or the growth medium containing the specimen to contact the sensor.

A variety of different fluorescent and visible pH indicators can be used as the active molecular species in pH or $CO_2$ sensors. Generally, the only limitations on the selection of indicators are the requirements that they have acceptable dynamic pH ranges and wavelength changes that are readily detectable by existing front surface fluorescence or reflectance technologies.

Sensors for detecting pH changes in the culture medium according to the invention preferably exhibit a change in fluorescence intensity or visible color over a pH range of about 5.0 to about 8.0.

Indicators for the $CO_2$ sensor should exhibit a change in fluorescence intensity or visible color preferably between about pH 13 and about 5, and most preferably between about pH 13 to about 9, in order to detect changes in $CO_2$ concentration.

Only certain pH indicator molecules can be bound covalently or non-covalently to a support medium and retain their pH indicating properties. Indicators belonging to the xanthene, phenolphthalein and phenolsulfonphthalein groups are useful. Examples of these include fluorescein, coumarin, phenolphthalein, thymolphthalein, bromothymol blue, thymol blue, xylenol blue and α-naphthol benzein.

The attachment/support medium can be a substance such as cellulose, to which a pH indicator can be covalently attached using organic reactions. Non-covalent attachment of pH indicators can be achieved using ionic support materials, such as nylon membranes that have a positive or negative zeta potential. Other ionic support materials that can be used are positive or negatively charged ionic resins, such as diethylamino ethyl (DEAE) resin or DEAE cellulose. Pretreatment of the support material with a protein may be required if the indicator membrane is to be in direct contact with the microbial growth medium.

The pH indicator sensors directly detect pH changes due to the pH environment of the microbial growth medium. However, these sensors can be made to selectively react to gases (e.g., carbon dioxide, ammonia) in the liquid growth medium by covering them with a selectively semi-permeable composition or membrane, such as silicone, latex, teflon, or various plastics characterized by the capacity to selectively permit the diffusion of a gas while preventing the passage of ions. For sensors comprising indicator encapsulated within a polymer matrix, the polymer forming the matrix can act as the semi-permeable barrier that permits the passage of gases but not ions.

In one embodiment, the $CO_2$ sensor is comprised of four components. The first component is a visual or fluorescent pH indicator, which is reactive at the pH range between 6 and 10. Examples of indicators meeting these criteria are bromothymol blue, thymol blue, xylenol blue, phenolphthalein, coumarin, and fluorescein. The second component is sodium hydroxide or an equivalent base, which maintains an optimal pH environment for detection of $CO_2$ by the selected pH indicator. The third component is glycerol or an equivalent emulsifier, which can produce droplets of indicator solution emulsified within the uncured polymer. The fourth component is the uncured polymer such as silicone, which maintains a proper environment for the indicator. Any polymer can be used that does not affect the chemical activity of the indicator, either from its own chemical or physical properties or its requirements for curing, as long as it is permeable to gases but not ions, and does not have these properties altered when subjected to sterilization. Other silicone polymers that are also satisfactory are those that are cured by high temperature, by catalytic activity, or by ultraviolet vulcanization. An emulsion is prepared from the four components and the polymer is cured to form a semipermeable matrix around the droplets of pH indicator, which permits selective diffusion of $CO_2$ and other gases from the liquid microbial growth medium, resulting in a measurable change in the indicator. The sensor can be prepared separately, such as in a mold, cured, and then attached to the culture bottle with an appropriate adhesive, such as a silicone adhesive. Alternatively, and preferably, the sensor is formed on the bottom of the bottle and cured in situ. After curing, the bottle with the sensor is sterilized, such as by autoclaving. Conveniently, the growth medium can be introduced into the bottle before autoclaving and also sterilized by that process.

The culturing of aerobic microorganisms requires a supply of oxygen within the culture bottle. The supply of oxygen can be from an amount of oxygen pumped into the culture bottle at the time of manufacture. Or, the culture bottle may be transiently vented or, a gas permeable membrane can be incorporated into the bottle to allow oxygen to pass into the bottle (without fluid passing out). Regardless of the way in which oxygen is supplied for microorganism growth, it is often desirable for the culture bottles to be agitated in some way to improve supply of oxygen to the liquid culture media. Also, with anaerobic microorganisms, agitation may be desirable to improve mixing.

Figure 5:
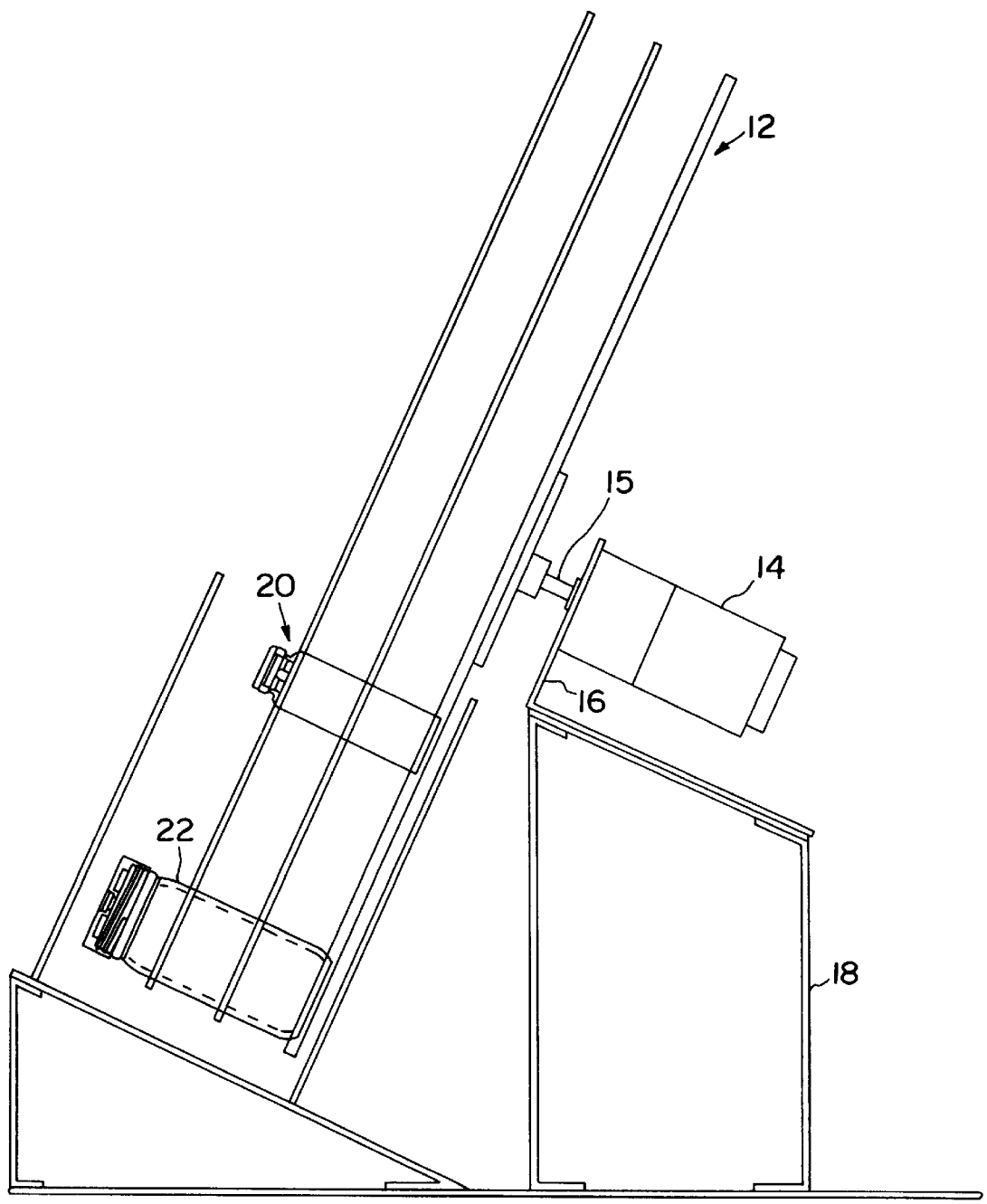

In the present invention, a rotary apparatus is provided for agitating containers for culturing microorganisms. As can be seen in FIG. 5, a wheel 12 is provided which, in the embodiment illustrated in this figure, is disposed at an angle of 25 degrees from vertical. Other angles at which the wheel can be disposed are possible, including anywhere from horizontal to vertical, though somewhere in between is preferred. A motor 14 held above base 18 by plate 16, rotates wheel 12 via a rotatable shaft 15. Culturing containers of different sizes, such as lesser diameter culturing bottles 20, or larger diameter culturing bottles 22, can be disposed for agitating within wheel 12.

Figure 6A:
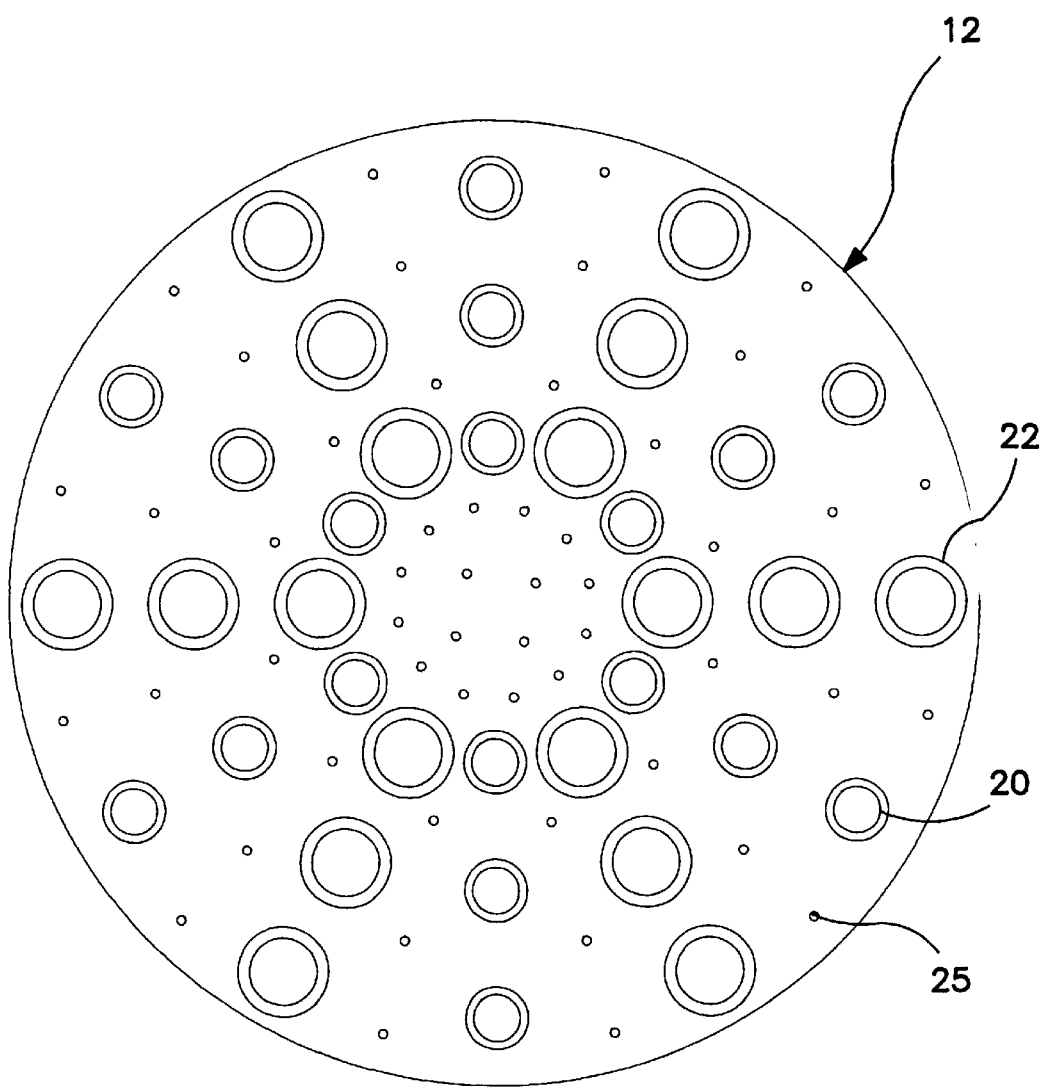
Figure 6B:
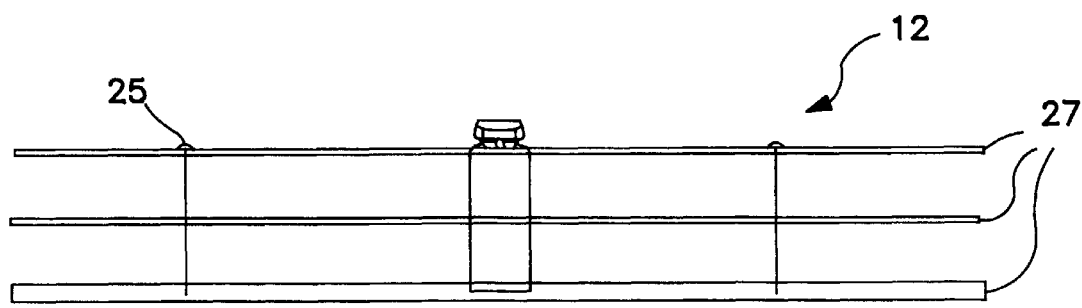

As can be better seen in a top view of wheel 12 in FIG. 6a, and a side view of wheel 12 in FIG. 6b, plates 27 which may be held together by, for example, screws 25, have a plurality of apertures (which may be of different sizes) for holding culturing containers. Coaxial apertures in each of plates 27 allow for a culturing container to be held within wheel 12. In another embodiment, a well is formed within wheel 12 with an optional transparent surface in the bottom-most plate of plates 27, to thereby hold a culturing container and contain spills should the culturing container crack or break.

As illustrated in FIG. 6a, culturing containers are disposed at three different radial distances from the center of wheel 12. In this way, as wheel 12 rotates, three different detectors disposed under wheel 12 at three different radial distances, are utilized for monitoring changes in the sensors disposed in the bottom of the culturing containers. Of course, if only the smaller diameter culturing containers are to be utilized, six culturing containers could be disposed along a single radius of wheel 12 (or more depending on the overall diameter of the wheel to be used). Culturing containers need not be disposed only along the same radii as illustrated in FIG. 6a, but rather, many more culturing containers can be disposed along the circumference as the distance from the center of the wheel increases. It is still desirable, however, to dispose the apertures/holders in wheel 12 in such a way as to maximize the number of culturing containers and minimize the number of sensors needed.

Figure 7:
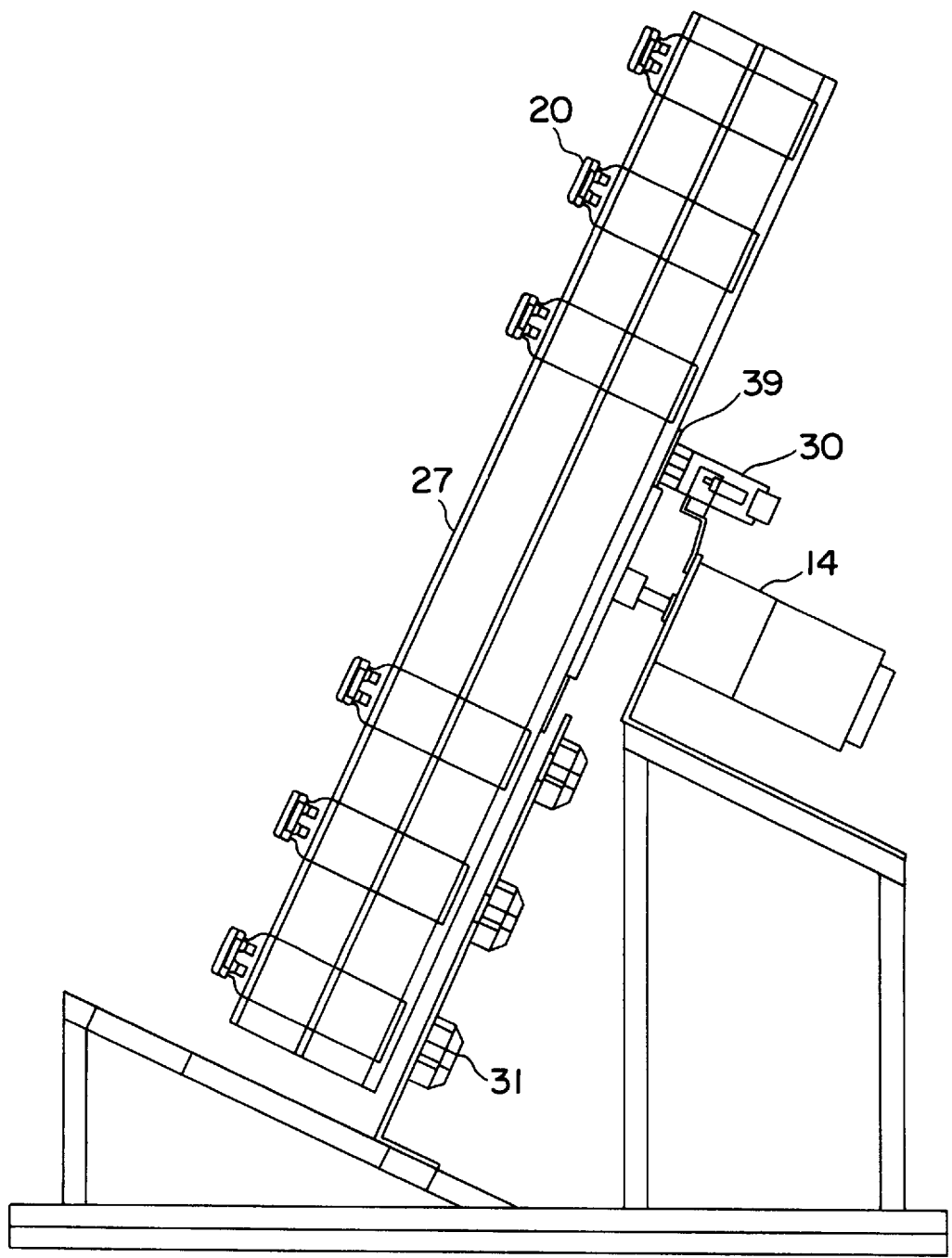

FIG. 7 is an illustration of a side view of the rotary culture apparatus. As can be seen in FIG. 7, culture bottles 20 are held perpendicularly to the polycarbonate disks 12, in this case at 25 degrees so that they are not inverted during rotation. As the culture bottles rotate, they sweep past the photodiode and LED array 31, the photodiode being triggered to acquire data by a photomicrosensor 30 emitting onto a rotary encoder wheel 39 on the back of the bottommost disk. A motor 14 rotates the polycarbonate disks holding the culture bottles, the transmittance of the sensor in the bottom of each bottle is read and this voltage signal is interpreted by software.

In FIG. 7, the polycarbonate disks are angled at 25 degrees from vertical so that the bottles, held perpendicularly to the disks, are at 25 degrees from horizontal. The disks can be tilted further from vertical depending on the bottles and the amount of fluid in the bottles.

Figure 8:
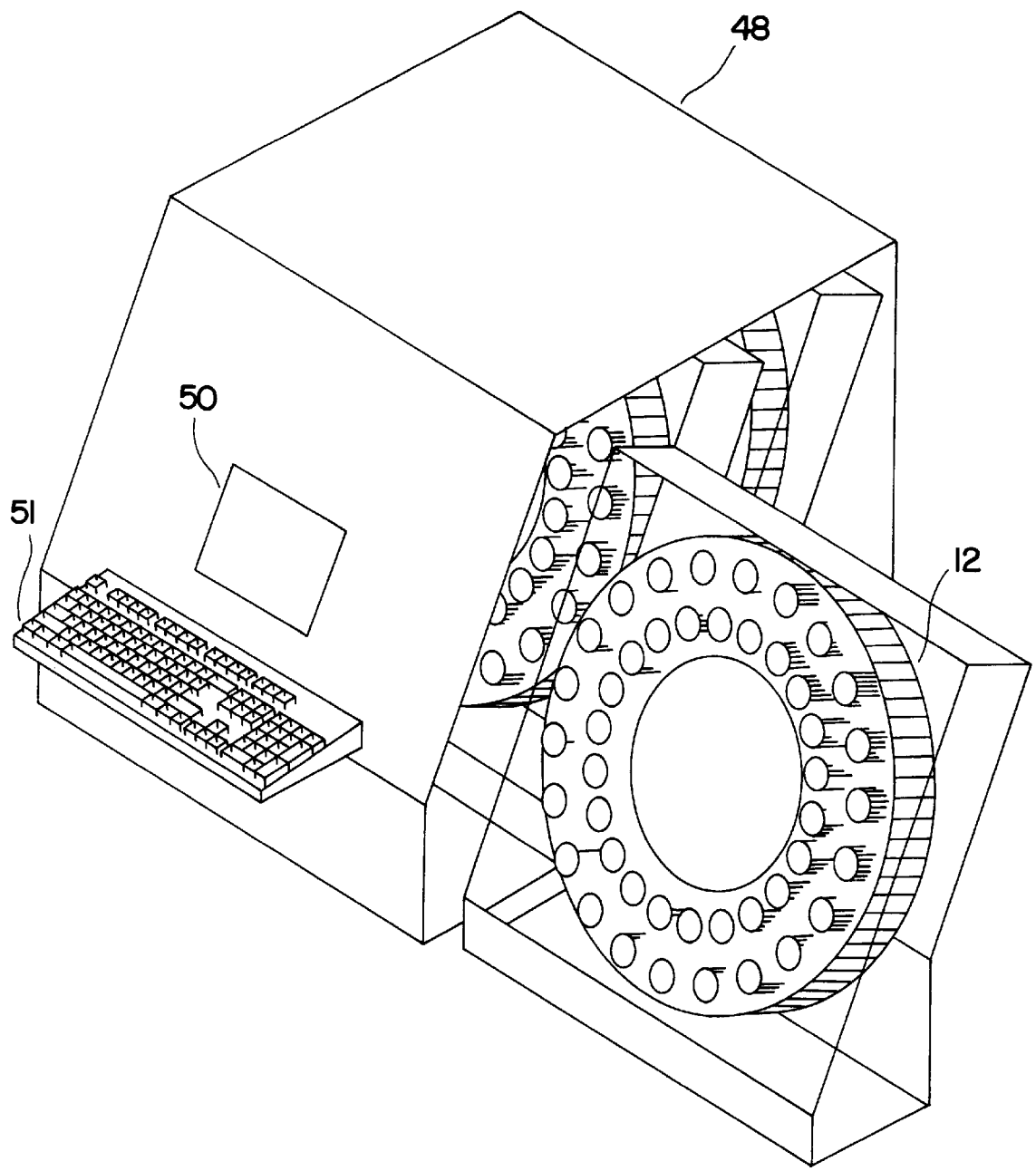

In FIG. 8, a plurality of wheels 12 are illustrated within a housing 48. A monitor 50 and keyboard 51 can also be provided for giving instructions and reading results of the culturing of the containers within the plurality of wheels 12. Preferably from one to six wheels are provided within housing 48.

An important feature of the present invention illustrated in FIGS. 5–8, is that the flat bottom of the culturing containers in which the sensor is disposed, always rotates within the same plane (that is, roughly within the plane defined by bottom disk 27, as illustrated in FIG. 6B). The angle of the sensor disk is always the same in relation to the detector. In this way, the sensor readings are less prone to error due to variations in alignment of the sensor disk during reading of the sensor by the detector. The error in the sensor signal can be large if the bottom of the culture bottle with the sensor proximate thereto, is not read in a constant position (e.g., directly perpendicular to the detector (photodiode)). It is estimated that only two degrees off of perpendicular can result in an error of 10% in the sensor reading. Also, in a number of embodiments of the present invention, the culture media is gently swirled. within the culture bottle, rather than shaken when the bottle is inverted. In addition, in the present invention a higher culturing bottle density is achievable compared to the prior art.

Though the culturing containers of the present invention may be held in place with clips, the containers may also further sit within a cell such that if a clip were to fail, a bottle would still remain within the cell and not drop out. Furthermore, in the embodiment of the invention of FIGS. 5–8, the bottles are not inverted such that there is a lesser chance of leakage out of the bottle via the cap. Also, should the bottle be in some way cracked or broken, material that might seep out of the bottle could be contained within the cell in which the bottle sits. This is particularly desirable should the bottle contain blood borne pathogens, and in particular pathogens which might be transmitted via an airborne aerosol.

In a second embodiment of the invention as illustrated in FIGS. 9a and 9b, the culture bottles may be held in place with clips/clamps attached to an upper portion of the bottle. This is similar to the arrangement in prior art rotary agitators. However, in the present invention, the orbit around which the bottles rotate, is not circular. Rather, it is important that at least a portion of the path along which the bottles travel is linear. In this way, as in the first embodiment of the present invention, the angles at which the bottoms 67 of the bottles; 22 extend as they pass the sensor are always perpendicular thereto. This results in sensor readings being less prone to errors due to variations in the alignment of the bottles. Of course, the arrangement in FIG. 10a can be stacked to result in a plurality of rows of culture bottles, each row having a corresponding detector for monitoring changes.

Figure 10:
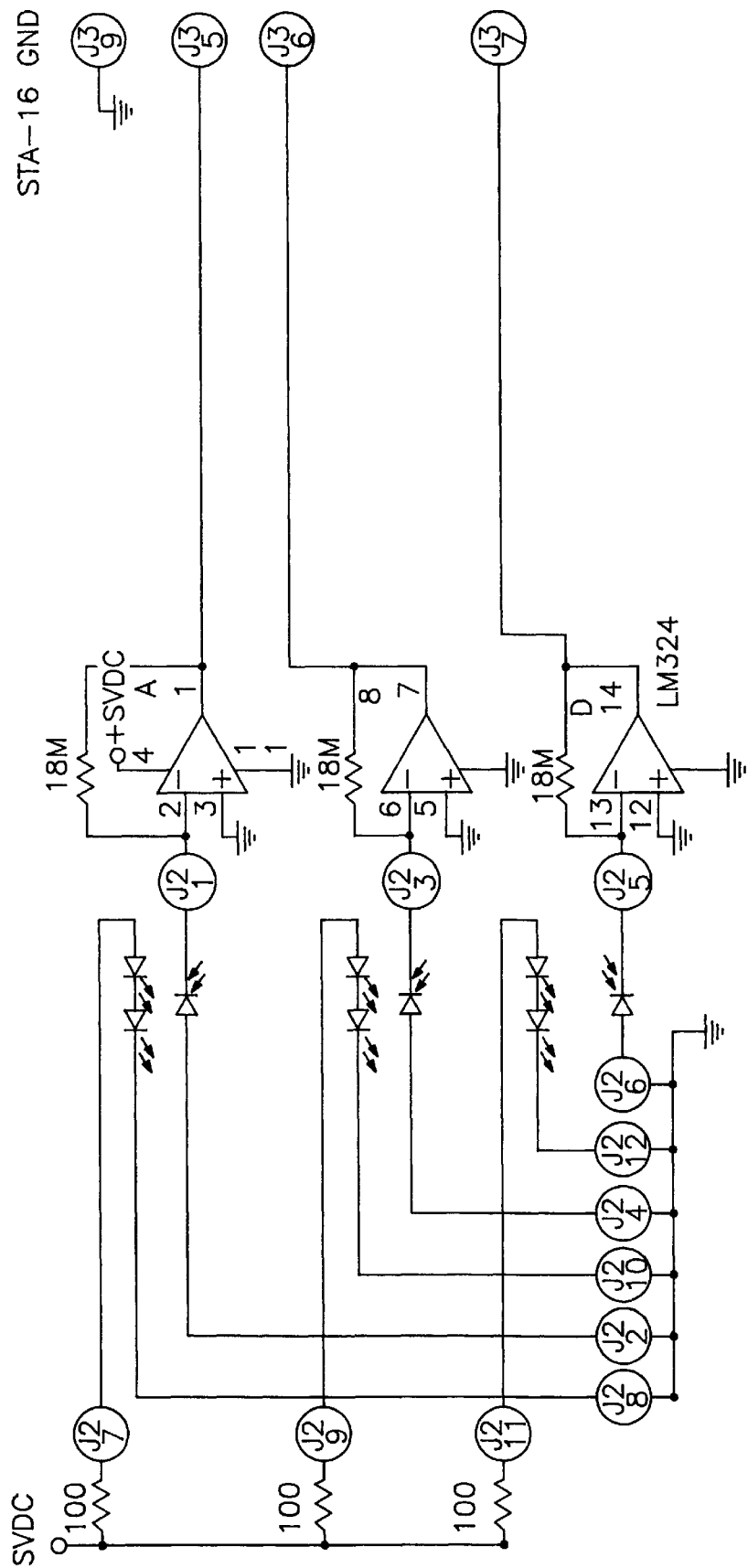

As the bottles rotate in their orbit, the bottom of each bottle, containing the sensor, passes across a photodiode (for example EG&G VACTEC VTB-5040) and a pair of LEDs (for example Hewlett Packard high efficiency red HLMP-3750). Light from the LED shines onto the sensor passing through the bottom of the transparent bottle. This light is transmitted back to the photodiode which produces a voltage signal and is amplified by, for example a photodiode amplifier circuit such as illustrated in FIG. 10 (e.g., Motorola quad amplifier, LM324). The signal, therefore, is a measure of the carbon dioxide in the bottle which is a measure of cellular respiration.

Figure 11:
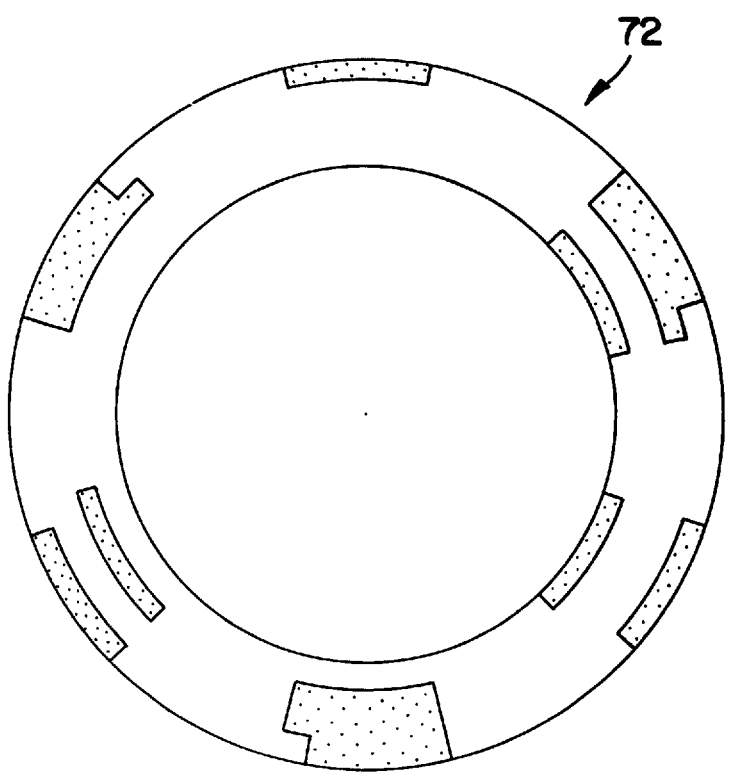
Figure 12:
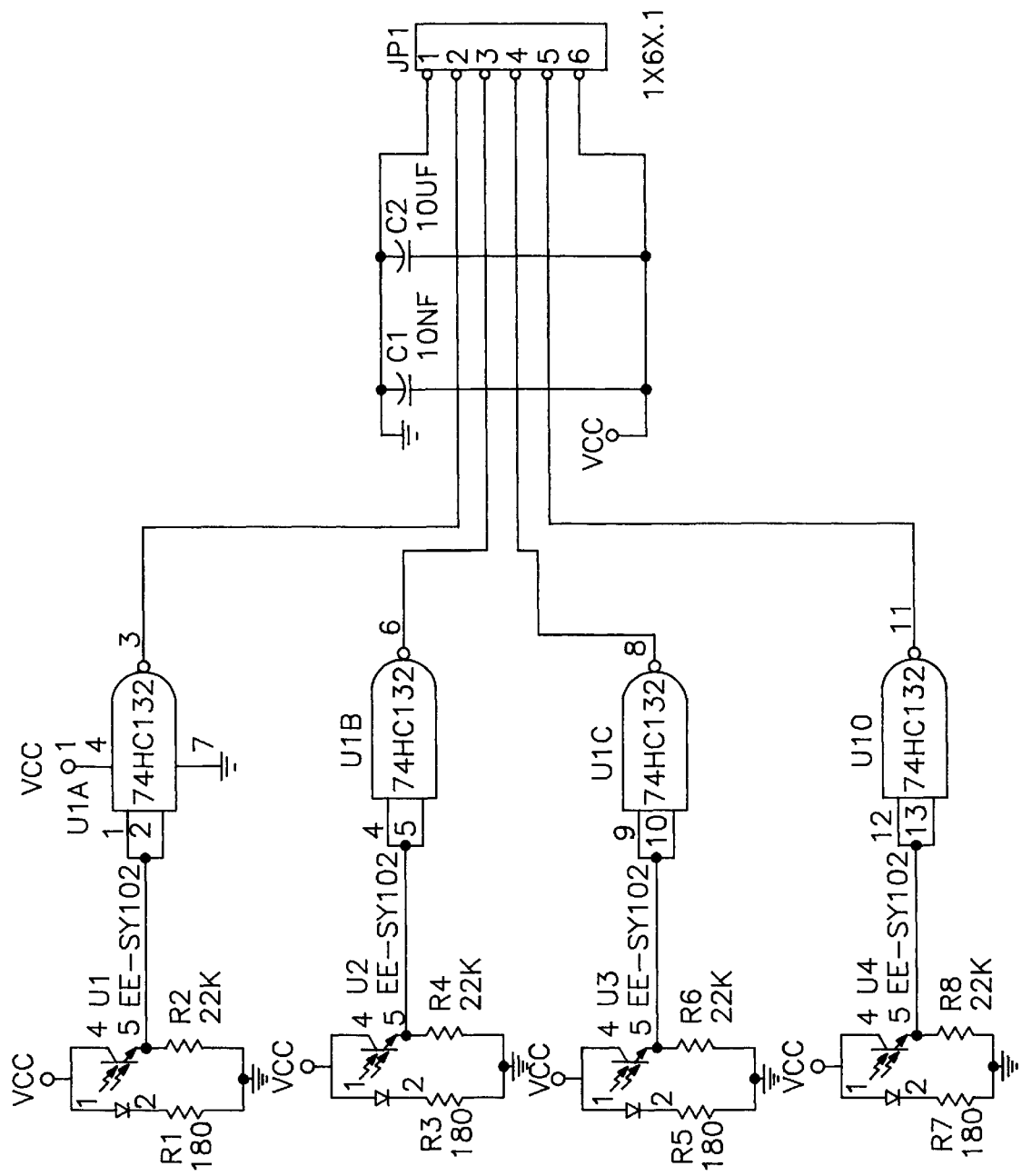

There is one photodiode/LED pair for each concentric ring of bottles. The backside of the bottom disk is painted black so that the transmitted light in the absence of bottles is very low, compared to the sensor. A rotary encoder 72 on the bottommost disk, such as illustrated in FIG. 11, encodes the bottle spokes in binary format, with this binary number being read by four photo microsensors (for example, OMRON EE-SY 102, see FIG. 12). This information is sent to a data acquisition board (for example Keithley Metrabyte DAS-16G) which can be connected to an IBM compatible PC. A software program keeps count of the number of revolutions and bottle positions.

If the sensor transmittance rises, the bottle can be determined to be positive for microbial growth, such that the software signals that there is a positive bottle and notifies the operator of its location on the wheel. At this time, it is possible to stop the motor so that the bottle can be removed for further tests. The instrument can then be restarted and the process repeated with a new bottle replacing the positive bottle, without disturbing the monitoring of the other bottles.

Figure 13:
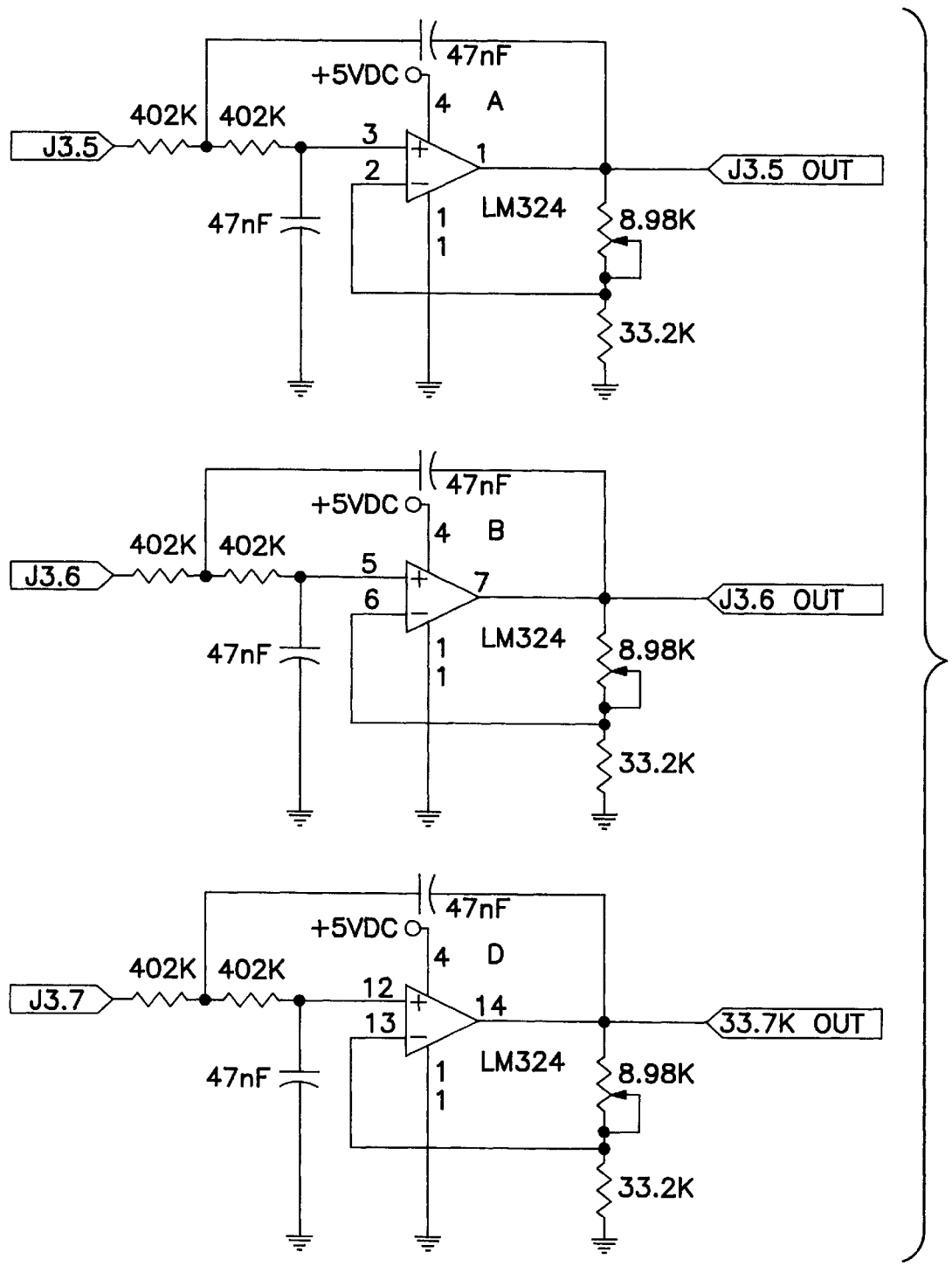

At ten revolutions per minute, the outer bottles pass across the photodiode in 50 ms. To eliminate line noise, but pass the sensor signal, an effective low-pass filter can be used, such as double-pole, equal-component, Bessel filter, such as illustrated in FIG. 13. This filter, due to a phase shift, introduces a delay which can be eliminated by physically shifting the optical encoder, thus triggering acquisition later by an amount equal to this delay.

The motor rotates the culture bottles at the desired speed. In one embodiment of the present invention, the culture bottles are rotated at 10 rpm. At this speed, the centrifugal force is much lower than the gravitational force such that fluid in the culture bottles is not thrown to the outer surface of the bottle. The bottles may be disposed within fluid hermetic cells and/or held in place with clips. Using clips to hold each bottle in place can be desirable such that the bottles do not spin within their respective positions.

As the motor rotates the culture bottles, the fluid in the bottles washes across the inner bottle surface. This effect improves aeration of the bottle since a small layer of fluid adheres to the bottle as it sweeps through its orbit. This increases the surface area of the fluid exposed to the air in the culture bottle and therefore improves the growth performance for aerobic organisms. For anaerobic organisms, the rotation of the bottle serves to mix the media therein.

At a predetermined interval, which may be ten minutes, the program signals that it is time to read the transmittance of the bottle sensors. The photodiode is triggered to read the sensor transmittance by the infrared object sensor which is triggered by the optical encoder. This encoder contains several rings, one ring is black indicating that there are bottles in that spoke, the other ring encodes the bottle position. With three rings, eight spoke positions can be encoded in binary form. Of course, more rings and spokes can be encoded with larger wheels. And, of course, other means for indicating whether a bottle is present or not, or, which bottle is which within the wheel, can be envisioned.

The sensor readings as constructed and as mentioned above, can be performed on the fly. In addition, there need not be a photodiode/LED pair for every bottle. Only one pair is required for each ring of bottles. The photodiode/LED pair can be calibrated automatically by standards painted onto the back of the bottom disk 27, eliminating the need for periodic QC by operators of the rotary mixer.

Figure 14:
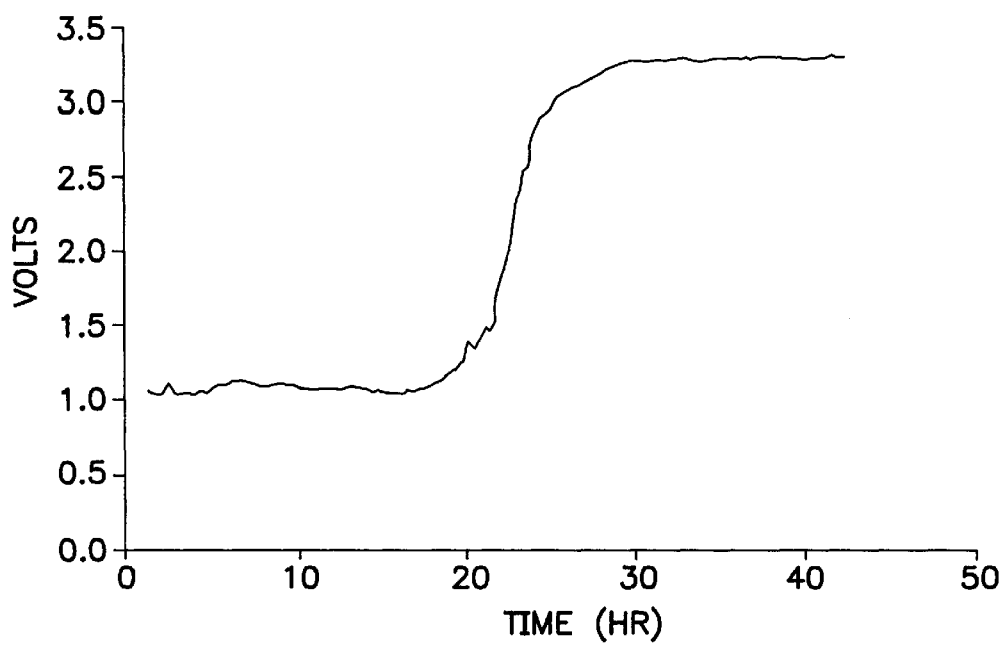

As can be seen in FIG. 14, *Candida albicans* was inoculated into a culture container. The sensor transmittance remained unchanged during the first fifteen hours, but then rose dramatically thereafter. *Candida albicans* produces a large amount of carbon dioxide resulting in a very large change in sensor transmittance. As seen in FIG. 14, a sensor reached a saturation point where more carbon dioxide produced did not change the transmittance, or depletion of nutrients in the media or depletion of the atmosphere resulted in a halt of organism growth. Organisms that produce lower amounts of carbon dioxide are not excluded from this instrument (see FIG. 15). High sensitivity is achieved with a proper analog filtering which can produce signal to noise ratios as high as 250 to 1.

Figure 15:
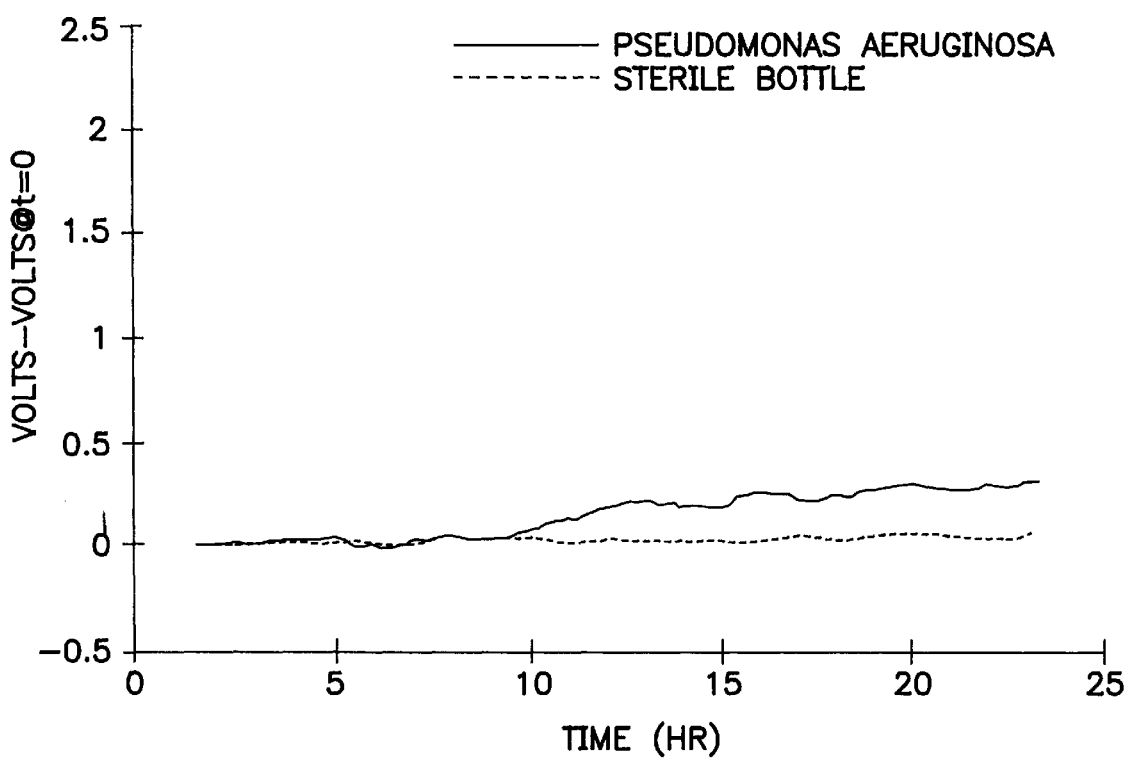

Even microorganisms which produce only a relatively small amount of carbon dioxide, can still be detected with the above-described system. As illustrated in FIG. 15, the growth of *Pseudomonas aeruginosa* is compared to base Line of a sterile bottle. FIG. 15 is a plot from a nine-point smoothed data of the average of three bottles.

Figure 16:
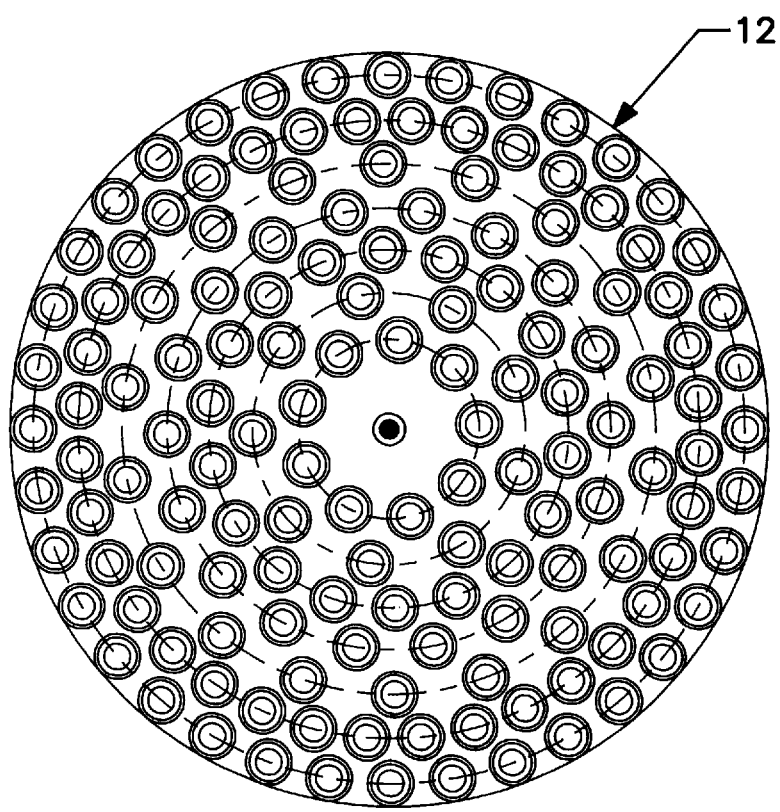

While preferred embodiments of the present invention as set forth herein, it is to be understood that modifications and variations may be utilized without departing from the scope of the present invention as set forth in the following claims. For example, though the wheel may be rotated at a constant speed, it may also be envisioned that the wheel is rotated at a first speed, and then at a slower speed for taking sensor readings of the bottles. After taking a set of readings, the angle of velocity could be increased. Also, though it is described above that the sensors are disposed along the flat bottom surface of the bottles, the sensors may also be disposed along the flat top surface of the caps of the bottles. And, though the bottles are illustrated in FIG. 6A as being relatively sparsely distributed, one of the advantages of the present invention as illustrated in FIG. 16, is that the density of distribution of the bottles within the wheel can be made high. In addition, though a central motor for rotating the wheel is described herein, it can be also envisioned that other means for rotating the wheel would be acceptable (e.g., bevel gears, worm gears or a rack and pinion gear system).

In any event, the preceding description is intended to be exemplary and should not be used to limit the scope of the invention.

We claim:

1. An instrument for monitoring microbial growth in a specimen in a sealable, sterilizable container, the instrument comprising:

a container having an internal chamber in which the specimen is cultured with a sterile culture medium, the container having at least one transparent section and a sterilizable indicator located in the container in the region of the transparent section, said indicator exhibiting a change in its measurable properties detectable through said transparent section upon exposure to changes within said container due to microbial growth, whereby changes in the indicator can be monitored from the exterior of the container through said transparent section, thereby monitoring microbial growth without entering the container after sealing, an emitter for emitting an emitter signal that interacts with at least one measurable property of said indicator, whereby an indicator signal is produced, said emitter positioned relative to said indicator so that said emitter signal strikes said indicator through the transparent section;

a detector positioned relative to said indicator for receiving the indicator signal from said indicator through the transparent section and for producing a detector signal corresponding thereto; and a processor for receiving said detector signal and for processing said detector signal to evaluate changes in or magnitude of the measurable property of said indicator and thereby monitoring microbial growth in said sealable container after said container has been sealed;

wherein, said instrument further comprises a measuring station at which the emitter and detector are located and a transport mechanism to transport said container in which the specimen is cultured to the measuring station for measuring changes in or magnitude of measurable properties of said indicator.

\* \* \* \* \*